United States Patent [19]

Hoskins et al.

[11] Patent Number: 4,491,539

[45] Date of Patent: Jan. 1, 1985

[54] LIQUID CLEANSING PRODUCT WITH SKIN FEEL ADDITIVES

[75] Inventors: James J. Hoskins; Adriaan Kessler, both of Cincinnati, Ohio

[73] Assignee: The Procter & Gamble Company, Cincinnati, Ohio

[21] Appl. No.: 488,921

[22] Filed: Apr. 27, 1983

Related U.S. Application Data

[63] Continuation-in-part of Ser. No. 460,211, Jan. 24, 1983, , which is a continuation of Ser. No. 270,436, Jun. 4, 1981, abandoned.

[51] Int. Cl.$^3$ .......................... C11D 1/83; C11D 3/37; C11D 3/46; C11D 17/08
[52] U.S. Cl. .................................. 252/541; 252/153; 252/173; 252/174.17; 252/174.18; 252/174.24; 252/548; 252/550; 252/551; 252/DIG. 2; 252/DIG. 5; 252/DIG. 13; 252/DIG. 14
[58] Field of Search .............. 252/173, 174.17, 174.18, 252/174.24, 541, 548, 550, 551, DIG. 2, DIG. 13, DIG. 14

[56] References Cited

U.S. PATENT DOCUMENTS

| | | | |
|---|---|---|---|
| 2,798,053 | 7/1957 | Brown | 260/2.2 |
| 3,591,680 | 7/1971 | Greene et al. | 424/156 |
| 3,697,644 | 10/1972 | Laiderman | 424/70 |
| 3,880,672 | 4/1975 | Megahed et al. | 136/111 |
| 3,939,260 | 2/1976 | Lafon | 424/28 |
| 3,984,342 | 10/1976 | Hall et al. | 252/186 |
| 4,113,854 | 9/1978 | Andrews et al. | 424/81 |
| 4,189,469 | 2/1980 | Gleixner et al. | 424/80 |
| 4,235,898 | 11/1980 | Watanabe | 252/154 |
| 4,414,144 | 11/1983 | Liebowitz | 252/548 |

FOREIGN PATENT DOCUMENTS 0067025 12/1982 European Pat. Off. .

OTHER PUBLICATIONS

Celanese Plastics: "Polymers For Personal Care Products—Application Bulletin DR–4930,2". (Publication date not established, but appears to be prior to 3–4–81).

Stein, Hall & Co.: *Jaguar Guar Gum & Guar Derivatives*, p. 30. (Publication date not established, but appears to be prior to 1981).

*Primary Examiner*—Dennis L. Albrecht
*Attorney, Agent, or Firm*—Richard C. Witte; John V. Gorman; Milton B. Graff

[57] ABSTRACT

Liquid cleansing products comprise about 5 to 30% of surfactant, about 0.1 to 1.0% of guar material, about 0.15 to 1.0% of carboxyvinyl polymer, and water.

25 Claims, No Drawings

LIQUID CLEANSING PRODUCT WITH SKIN FEEL ADDITIVES

CROSS-REFERENCE TO RELATED APPLICATION

This application is a continuation-in-part of co-pending application Ser. No. 460,211, filed Jan. 24, 1983 in the names of the present Applicants.

TECHNICAL FIELD

This invention relates to liquid cleansing products and, more specifically, to liquid cleansing products which provide beneficial skin feel properties to the product.

BACKGROUND OF THE INVENTION

Liquid cleansing products are extensively used as hand cleaners, shampoos, and for many other purposes. The current invention is concerned primarily with cleansers used for cleaning skin but is not limited to that application. The cleansers of interest are aqueous based and contain surfactant.

In order to achieve controlled use of a liquid cleansing product, it is desirable to have a viscous but pourable or pumpable product. A thin, watery product is too easily spilled and wasted when used and does not have good consumer acceptance. Guar gum and its chemically modified derivatives are well known product ingredients used in a wide variety of aqueous based products and are described variously as thickeners, gelling agents, suspending agents, protective colloids, binder materials, agglomerating agents, etc. As used herein, the term "guar material" is used to denote guar gum or derivatives produced by chemically modifying guar gum unless specifically noted otherwise.

In the present invention, guar materials have been found to be effective as thickening agents in liquid cleanser formulations. In addition, it has been found that guar material, and particularly certain derivatives of guar gum, imparts a desirable smooth, slippery skin feel to the liquid cleansing products. However, cleansing products formulated with the levels of guar material needed to provide the desired thickening and skin feel properties are not stable, but tend to separate. A thick paste, presumably high in guar material content, settles to the bottom of the product container. The addition of carboxyvinyl polymer to such cleansing product formulations has been found to substantially reduce or completely eliminate such separation.

Carboxyvinyl polymers are a family of acrylic acid copolymers marketed by the B. F. Goodrich Company, New York, N.Y. under the tradename of Carbopol. Carboxyvinyl polymers are well known ingredients that impart many of the same functional benefits as guar materials to aqueous based compositions. In fact, carboxyvinyl polymers and guar materials are often indicated as being interchangeable ingredients in particular formulations. For example, in U.S. Pat. No. 3,697,644 issued to Laiderman on Oct. 10, 1972, carboxypolymethylene (a carboxyvinyl polymer, Carbapol 934) and guar gum (a guar material, Jaguar A-20-D from Stein, Hall and Company) are specified as alternative thickening agents which act as a protective colloid to hold a dispersed phase in suspension in cosmetic compositions. In U.S. Pat. No. 3,939,260 issued Feb. 17, 1976, to Lafon, Carbopol and guar gum are used alternatively as a thickener or binder in therapeutic and cosmetic compositions.

In U.S. Pat. No. 3,591,680 issued to Green et al. on July 6, 1971, the use of Carbopol or guar gum as a suspending agent in antacid compositions is disclosed. Guar gum or Carbopol can be used as a binder material in producing a battery gel substance in U.S. Pat. No. 3,880,672 issued to Megahead et al. on Apr. 29, 1975. Green and Megahead consider guar gum and carboxyvinyl polymer to be different materials that can be used interchangeably for the same purpose along with a number of other materials. These references regard the individual materials or any combination of them to be the same. Neither reference specifically discloses a combination of carboxyvinyl polymer and guar gum, and neither suggests that such a combination might have more desirable properties than either used separately in a liquid skin cleanser.

It is therefore an object of the present invention to provide liquid cleansing compositions which deliver good skin feel and are stable.

It is a further object of the present invention to provide liquid cleansing compositions which utilize particular levels of a guar material and a carboxyvinyl polymer.

These and other objects will become apparent from the following detailed description. All percentages herein are by weight unless otherwise specified.

SUMMARY OF THE INVENTION

The invention described herein is a liquid cleansing product comprising from about 5 to 30% of surfactant, from about 0.1 to 1.0% of guar material, from about 0.15 to 1.0% of carboxyvinyl polymer, and water.

DETAILED DESCRIPTION OF THE INVENTION

This invention relates to liquid cleansing products that utilize a combination of guar material and carboxyvinyl polymer to achieve a shelf stable, thickened product with superior skin feel characteristics. The liquid cleansing products of this invention are aqueous based formulations containing surfactant, guar material, and carboxyvinyl polymer. Preferred liquid cleansing products also contain, as minor ingredients, compounds which function as opacifiers, perfumes, colorants, preservatives, and pH adjusters. The necessary and optional ingredients are described in detail below.

Guar Material

In the present liquid cleansing products it has been found that guar material can provide a highly desirable smooth, slippery skin feel to the products. Guar gum is a naturally occurring material which is the principal component of the seed of the guar plant. Guar gum is extracted from the guar seed and purified. Guar gum is a high molecular weight carbohydrate polymer or polysaccharide made up of mannose and galactose units linked together. The guar molecule is essentially a straight chain of mannose units linked to each other by means of beta (1–4) glycosidic linkages. Galactose units branch from alternate mannose units through alpha (1–6) linkages with the mannose units.

The desired skin feel of the liquid cleansing products is preferably obtained by using hydroxypropyl guar gum. In the guar gum molecule, each mannose and galactose unit has from 2–4 hydroxyl groups depending on where it is located in the polymer chain. Guar gum derivatives are produced by reacting guar gum such that substitution of chemical moities occurs on some of these hydroxyl units. Hydroxypropyl guar gums are a family of materials with hydroxypropyl groups substituted for some of the hydroxyl units. The term "degree of substitution" is used to indicate the average number of hydroxypropyl units which occur on each of the sugar units in the polymer molecule. It is preferred that the hydroxypropyl guar gum used in the present invention have a degree of substitution of from 0 to about 1.2; more preferred is hydroxypropyl guar gum with a degree of substitution of from about 0.3 to about 0.8; especially preferred is hydroxypropyl guar gum with a degree of substitution of about 0.6. Such materials are available commercially from Celanese Plastics & Specialties Company, Louisville, Kentucky: Jaguar HP-11 has a degree of substitution of about 0.35 to 0.45; Jaguar HP-60 has a degree of substitution of about 0.6; Jaguar HP-80 has a degree of substitution of about 0.8.

The quantity of guar gum material used in the liquid cleansing products of this invention is from about 0.1% to about 1.0%. A preferred range of usage for hydroxypropyl guar gum is from about 0.2% to about 0.5%; especially preferred is about 0.3%. A preferred range of usage for guar gum is from about 0.1% to about 0.3%.

Carboxyvinyl Polymer

Although guar gum material alone will provide the desired skin feel in liquid cleansing products, it was found that such products are not shelf stable. In time, a viscous layer, presumably high in guar material content, settles to the bottom of the product container. It was found that the addition of carboxyvinyl polymer to the liquid cleansing products provided shelf stable products while retaining the desired superior skin feel properties.

The term "carboxyvinyl polymer" as used herein describes a family of compounds disclosed and claimed in U.S. Pat. No. 2,798,053 issued on July 2, 1957, to Brown, the specification of which is hereby incorporated by reference. Methods for making carboxyvinyl polymers are also disclosed in Brown.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

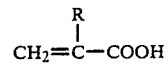

where R is a substituent selected fom the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

Various carboxyvinyl polymers are commercially available from B. F. Goodrich Company, New York, N.Y., under the tradename Carbopol. Carboxyvinyl polymers found to stabilize cleansing product formulations of the present invention include Carbopol 910 having a molecular weight of about 750,000, preferred Carbopol 941 having a molecular weight of about 1,250,000, and highly preferred Carbopols 934 and 940 having molecular weights of about 3,000,000 and 4,000,000, respectively.

Highly preferred Carbopol 934 is a very slightly cross-linked carboxyvinyl polymer having a molecular weight of about 3,000,000. It has been described as a high molecular weight polyacrylic acid cross-linked with about 1% of polyallyl sucrose having an average of about 5.8 allyl groups for each molecule of sucrose.

The quantity of carboxyvinyl polymer used in the liquid cleansing products of this invention is from about 0.15% to about 1.0%. A preferred range of usage is from about 0.2 to about 0.5%; especially preferred is about 0.35%.

Surfactant

The liquid cleansing products of this invention contain a surfactant system comprising one or more surfactants.

The surfactants suitable herein are water soluble foaming organic detergents selected from anionic, nonionic, cationic, zwitterionic and amphoteric classes. Suitable detergent materials are those which provide copious suds formation and cleansing properties. Examples of surfactant materials form which the liquid cleansing products of the invention can be selected include the water soluble anionic, nonionic, cationic, zwitterionic and amphoteric detergents described as follows:

a. Anionic detergents include the synthetic non-soap detergents which can be broadly described as the water-soluble salts, particularly the alkali metal and ammonium salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the synthetic detergents which form a part of the compositions of the present invention are the alkali metal, e.g. sodium or potassium, and ammonium alkyl sulfates, especially those obtained by sulfating the higher alcohols ($C_8$–$C_{18}$ carbon atoms) produced by reducing the glycerides of tallow or coconut oil; the alkali metal olefin sulfonates, of from 8 to 24 carbon atoms described, for example, in U.S. Pat. No. 3,332,880, issued July 25, 1967 to Philip E. Pflaumer and Adriaan Kessler; and the alkali metal alkyl glyceryl ether sulfonates, especially those ethers of the higher alcohols derived from tallow and coconut oil; other anionic detergents include the alkali metal alkylbenzene sulfonates, in which the alkyl group contains from about 9 to about 15 carbon atoms, including those of the types described in U.S. Pat. Nos. 2,220,099 and 2,477,383 (the alkyl radical can be a straight or branched aliphatic chain); sodium coconut oil fatty acid monoglyceride sulfates and sulfonates; sodium, potassium, or ammonium salts of sulfuric acid esters of the reaction product of one mole of a higher fatty alcohol (e.g., tallow or coconut oil alcohols) and about 1 to 12 moles of ethylene oxide (hereinafter referred to as "alkali metal or ammonium alkyl ethoxy sulfates"); sodium or potassium salts of alkyl phenol ethylene oxide ether sulfate with about 1 to about 10 units of ethylene oxide per molecule and in which the alkyl radicals contain from 8 to about 12 carbon atoms; the reaction product of fatty acids esterified with isethionic acid and neutralized with sodium hydroxide where, for example, the fatty acid is oleic or derived from coconut oil; sodium or potassium salts of fatty acid amide of a methyl tauride in which the fatty acids, for example, are derived from coconut oil, sodium or potassium β-acetoxy-or β-acetamidoalkane-sulfonates where the alkane has from 8 to 22 carbon atoms; and others known in the art, a number specifically set forth in U.S. Pat. Nos. 2,486,921, 2,486,922 and 2,396,278.

b. Nonionic synthetic detergents: One class can be broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Another class has semi-polar characteristics. Classes of nonionic synthetic detergents are as follows:

1. The monoethanol, diethanol, and ammonia amides of fatty acids having an acyl moiety of from about 8 to about 18 carbon atoms. These acyl moieties are normally derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process.

2. A class of nonionic synthetic detergents under the trade name of "pluronic". These compounds are formed by condensing ethylene oxide with a hydrophobic base formed by the condensation of propylene oxide with propylene glycol. The hydrophobic portion of the molecule which, of course, exhibits water insolubility, has a molecular weight of from about 1500 to 1800. The addition of polyoxyethylene radicals to this hydrophobic portion tends to increase the water solubility of the molecule as a whole and the liquid character of the product is retained up to the point where the polyethylene content is about 50% of the total weight of the condensation product.

3. The polyethylene oxide condensates of alkyl phenols, e.g., the condensation products of alkyl phenols having an alkyl group containing from about 6 to 12 carbon atoms in either a straight chain or branched chain configuration with ethylene oxide, the said ethylene oxide being present in amounts equal to 5 to 25 moles of ethylene oxide per mole of alkyl phenol. The alkyl substituent in such compounds may be derived from polymerized propylene, diisobutylene, octene, or nonene, for example.

4. Those nonionic synthetic detergents derived from the condensation of ethylene oxide with the product resulting from the reaction of propylene oxide and ethylene diamine. For example, compounds containing from about 40 to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide; said base having a molecular weight of the order of 2,500 to 3,000 are satisfactory.

5. The condensation product of aliphatic alcohols having from 8 to 22 carbon atoms, in either straight chain or branched chain configuration, with ethylene oxide, e.g., a coconut alcohol ethylene oxide condensate having from 5 to 30 moles of ethylene oxide per mole of coconut alcohol, the coconut alcohol fraction having from 10 to 14 carbon atoms.

6. Long chain tertiary amine oxides corresponding to the following general formula

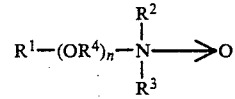

wherein $R^1$ is an alkyl radical of from about 8 to about 24 carbon atoms, $R^2$ and $R^3$ are each methyl, ethyl or hydroxyethyl radicals, $R^4$ is ethylene, and n equals from 0 to about 10. The arrow in the formula is a conventional representation of a semi-polar bond. Specific examples of amine oxide detergents include: dimethyldodecylamine oxide; cetyldimethylamine oxide; bis-(2-hydroxyethyl) dodecylamine oxide; and bis-(2-hydroxyethyl)-3-dodecoxy-1-hydroxypropyl amine oxide.

7. Long chain tertiary phosphine oxides, corresponding to the following general formula RR'R''P→O wherein R is an alkyl, alkenyl or monohydroxyalkyl radical ranging from 10 to 24 carbon atoms in chain length and R' and R'' are each alkyl or monohydroxyalkyl groups containing from 1 to 3 carbon atoms. The arrow in the formula is a conventional representation of a semi-polar bond. Examples of suitable phosphine oxides are found in U.S. Pat. No. 3,304,262 of Feb. 14, 1967 and include: dimethyldodecylphosphine oxide; diethyldodecylphosphine oxide; dimethyl-(2-hydroxydodecyl) phosphine oxide.

8. Long chain sulfoxides having the formula

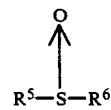

wherein $R^5$ is an alkyl radical containing from about 10 to about 28 carbon atoms, from 0 to about 5 ether linkages and from 0 to about 2 hydroxyl substituents, at least one moiety of $R^5$ being an alkyl radical containing 0 ether linkages and containing from about 10 to about 18 carbon atoms, and wherein $R^6$ is an alkyl radical containing from 1 to 3 carbon atoms and from one to two hydroxyl groups. Specific examples of these sulfoxides are: dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

c. Amphoteric synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition or sodium-3-dodecylaminopropionate and sodium-3-dodecylaminopropane sulfonate.

d. Zwitterionic synthetic detergents can be broadly described as derivatives of aliphatic quaternary ammonium, phosphonium, and sulfonium compounds, in which the aliphatic radical may be straight chain or branched, and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are 3-(N,N-dimethyl-N-hexadecylammonio) propane-1-sulfonate and 3-(N,N-dimethyl-N-hexadecylammonio)-2-hydroxy propane-1-sulfonate.

e. Cationic detergents include those having the formula $R-N(R^2)_3^{(+)}X^{(-)}$ wherein R is an alkyl chain containing from about 8 to about 20 carbon atoms, each $R^2$ is selected from the group consisting of alkyl and alkanol groups containing fom 1 to 4 carbon atoms and benzyl groups there being normally no more than one benzyl group and two $R^2$ groups can be joined by either a carbon-carbon ether, or imino linkage to form a ring structure, and X represents a halogen atom, sulfate group, nitrate group or other pseudohalogen group. Specific examples are coconut alkyl trimethyl amine chloride, dodecyl dimethyl benzyl bromide, and dodecyl methyl morpholino chloride.

A water-soluble surfactant is employed in the invention in an amount sufficient to provide desired suds formation and cleaning under normal usage conditions. In some instances copious suds formation will be desired while in others a composition providing less sudsing may be preferred by the user. Depending upon the foaming capacity and amounts of the particular detergents employed, desirable variations can be obtained. Normally the surfactant will comprise from about 5% to about 30% by weight of the composition. Preferably, the surfactant comprises from about 10% to about 25% by weight of the composition; especially preferred is about 15–20% by weight surfactant in the liquid cleansing products.

Preferred surfactants for use in the liquid cleansing products include the alkali metal or ammonium alkyl sulfates, alkali metal or ammonium alkyl ethoxy sulfates, and monoethanol and diethanol amides of fatty acids described hereinabove, and mixtures thereof. Especially preferred is a mixture of sodium alkyl sulfate, sodium alkyl ethoxy (3) sulfate, and coconut monoethanol amide.

Optional Ingredients

Where the composition of a liquid cleansing product will be in contact with the skin of the users, it is preferred that the cleansing product be formulated to provide a pH in use within the range of from about 4 to about 10, depending upon the particular surfactant or materials employed. Especially preferred is a pH in the range of 6 to 7. Any of a large number of known substances can be used to adjust the pH of the liquid cleansing product, e.g., sodium hydroxide, citric acid, generally at a level of up to about 0.5% of the product composition.

Materials that provide skin conditioning benefits such as humectants, e.g., glycerin, may be added to the liquid cleansing products of the present invention, generally at a level of about 1% to about 8% of the product composition. Perfumes may be used in formulating the liquid cleansing products, generally at a level of about 0.1% to about 1.0% of the product composition. Colorants may also be used in the liquid cleansing products. Opacifiers, e.g., ethylene glycol distearate, polystyrene latex, generally at a level of about 0.2% to about 2.0% of the product composition, may be used in the liquid cleansing products to provide them with an opaque or pearlescent appearance. Preservatives, e.g., EDTA, methyl paraben, propyl paraben, Germall 115, Kathon, generally at a level of less than 1%, may be incorporated in the liquid cleansing products to prevent microbiological growth in the products.

The liquid cleansing products of the present invention contain from about 60% to about 95% water, preferably from about 70% to about 90% water.

Method of Manufacture

A method of making liquid cleansing products of the present invention is described in Example 1 which follows.

Industrial Applicability

The liquid cleansing products of the present invention are designed primarily for the cleaning of human skin; they are expected to be used especially for the washing of hands.

The following examples will illustrate the invention, but are not intended to be any way limiting thereof.

EXAMPLE 1

| Component | Amount |
| --- | --- |
| sodium $C_8$ to $C_{18}$ alkyl sulfate | 7.2% |
| sodium $C_8$ to $C_{18}$ alkyl ethoxy(3) sulfate | 8.8% |
| coconut monoethanol amide | 4.0% |
| Jaguar HP-60 | 0.30% |
| Carbopol 934 | 0.35% |
| perfumes, colorants, preservatives, opacifiers and pH adjusters | less than 3% |
| water | balance |

A liquid cleansing product of the above composition was produced by a batch process comprising the following steps:

1. A Carbopol premix solution was prepared by adding the Carbopol slowly to water being agitated. After the Carbopol was dissolved, the solution was heated to about 135° F. (57° C.) to 150° F. (65° C.).

2. Water was added to the batch mix tank and the anionic surfactants were added to it. The solution was heated to about 150° F. (65° C.).

3. Preservatives and nonionic surfactant were added to the batch mix tank with agitation.

4. A guar material premix solution was prepared by adding the guar material to water that had been made alkaline by the addition of a small quantity of soduim hydroxide.

5. The guar material solution was added to the batch mix tank with agitation such that good dispersion of the guar material solution was assured.

6. The colorant, the Carbopol solution, and then the opacifier were added to the batch mix tank with agitation.

7. The contents of the batch mix tank were cooled to below 135° F. (57° C.), the perfume was added, and the pH was adjusted to between 6 and 7 by the addition of a small quantity of citric acid or sodium hydroxide. Cooling was continued until the product temperature was below 90° F. (32° C.).

EXAMPLE 2

| Component | Amount |
| --- | --- |
| sodium $C_8$ to $C_{18}$ alkyl sulfate | 8.0% |
| sodium $C_8$ to $C_{18}$ alkyl ethoxy(12) sulfate | 8.0% |
| coconut monoethanol amide | 2.0% |
| glycerine | 2.0% |
| Jaguar HP-11* | 0.30% |
| Carbopol 934 | 0.30% |
| preservatives, opacifiers, colorants, perfumes, and pH adjusters | less than 3% |
| water | balance |

*Hydroxypropyl guar gum with a degree of substitution of about 0.35–0.45 from Celanese Plastics & Specialties Company.

A liquid cleansing product is made with the composition above using the process described in Example 1. Glycerine is added to the batch mix tank in step 3.

EXAMPLE 3

| Component | Amount |
| --- | --- |
| ammonium $C_8$ to $C_{18}$ alkyl sulfate | 5.0% |
| ammonium $C_8$ to $C_{18}$ alkyl ethoxy(3) sulfate | 7.8% |
| coconut monoethanol amide | 4.0% |
| Jaguar HP-60 | 0.35% |
| Carbopol 934 | 0.35% |
| perfumes, colorants, preservatives, opacifiers and pH adjusters | less than 3% |
| water | balance |

A liquid cleansing product of the above composition is made by the process described in Example 1.

EXAMPLE 4

| Component | Amount |
| --- | --- |
| ammonium $C_8$ to $C_{18}$ alkyl sulfate | 5.5% |
| ammonium $C_8$ to $C_{18}$ alkyl ethoxy(3) sulfate | 5.6% |
| coconut monoethanol amide | 1.0% |
| coconut fatty acid | 1.0% |
| Jaguar HP-60 | 0.30% |
| Carbopol 934 | 0.25% |
| perfumes, colorants, preservatives, opacifiers and pH adjusters | less than 3% |
| water | balance |

A liquid cleansing product of the above composition is made by the process described in Example 1.

EXAMPLE 5

| Component | Amount |
| --- | --- |
| sodium $C_8$ to $C_{18}$ alkyl sulfate | 7.2% |
| sodium $C_8$ to $C_{18}$ alkyl ethoxy(3) sulfate | 8.8% |
| coconut monoethanol amide | 4.0% |
| Jaguar A-40-F* | 0.60% |
| Carbopol 934 | 0.35% |
| perfumes, colorants, preservatives, opacifiers and pH adjusters | less than 3% |
| water | balance |

*Purified guar gum from Celanese Plastics & Specialties Co.

A liquid cleansing product of the above composition is made by the process described in Example 1.

EXAMPLE 6-19

Liquid cleansing product Examples 6-19 were made according to the process described in Example 1. Each of these Examples contained 7.2% sodium $C_8$ to $C_{18}$ alkyl sulfate, 8.5% sodium $C_8$ to $C_{18}$ alkyl ethoxy(3) sulfate, 4.0% coconut monoethanol amide, guar gum material as indicated in the Table below, carboxyvinyl polymer material as indicated in the Table below and water. The pH of the liquid cleansing products was adjusted to 6.8 for each Example by the addition of small amounts of sodium hydroxide or citric acid as needed. Portions of Examples 6-19 were stored for four weeks at 80° F. and 100° F. The storage test results of these Examples, presented in the Table below, demonstrate the stabilizing effect achieved with a wide variety of carboxyvinyl polymers on liquid cleansing product formulations containing guar gum and hydroxypropyl guar gums having varying degrees of substitution.

TABLE

| Example | JAGUAR* Type | A-mount | CARBOPOL** Type | Amount | Stability 80° F. | 100° F. |
| --- | --- | --- | --- | --- | --- | --- |
| 6 | HP-60 | 0.3% | 934 | 0.25% | Uniform | Uniform |
| 7 | HP-60 | 0.3% | — | 0% | Separated | Separated |
| 8 | HP-60 | 0.3% | 940 | 0.3% | Uniform | Uniform |
| 9 | HP-60 | 0.3% | 941 | 0.3% | Uniform | Uniform |
| 10 | HP-60 | 0.3% | 910 | 0.3% | Uniform | Sl. Sep. |
| 11 | HP-80 | 0.5% | 934 | 0.15% | Uniform | Uniform |
| 12 | HP-80 | 0.5% | — | 0% | Separated | Separated |
| 13 | HP-11 | 0.2% | 934 | 0.15% | Uniform | Uniform |
| 14 | HP-11 | 0.2% | — | 0% | Separated | Separated |
| 15 | A-40-F | 0.2% | 934 | 0.4% | Uniform | Uniform |
| 16 | A-40-F | 0.2% | — | 0% | Separated | Separated |
| 17 | HP-60 | 0.2% | 934 | 0.15% | Uniform | Uniform |
| 18 | HP-60 | 0.2% | — | 0% | Separated | Separated |
| 19 | HP-60 | 0.1% | 934 | 0.15% | Sl. Sep. | Uniform |

*Guar gum materials commercially available from Celanese Plastics & Specialties Co., Louisville, Kentucky.
**Carboxyvinyl polymers commercially available from B. F. Goodrich Co., New York, New York.

While particular embodiments of the present invention have been illustrated and described, it would be obvious to those skilled in the art that various changes and modifications can be made without departing from the spirit and scope of the invention. It is intended to cover, in the appended claims, all such modifications that are within the scope of this invention.

What is claimed is:

1. A liquid cleansing product having desirable skin feel characteristics and having good stability against phase separation, said product comprising:
   (a) from about 5% to about 30% of surfactant;
   (b) from about 0.1% to about 1.0% of guar gum material selected from the group consisting of guar gum and hydroxypropyl guar gum;
   (c) from about 0.15% to about 1.0% of carboxyvinyl polymer having a molecular weight of at least about 750,000, said carboxyvinyl polymer comprising an interpolymer of a monomeric mixture comprising a monomeric polymerizable, alpha-beta monoolefinically unsaturated lower aliphatic carboxylic acid, and from about 0.1% to about 10% by weight of the total monomers of a polyether of a polyol selected from the class consisting of oligosaccharides, reduced derivatives thereof in which the carbonyl group is converted to an alcohol group, and pentaerythritol, the hydroxyl groups of said polyol which are modified being etherified with allyl groups said polyol having at least two allyl ether groups per polyol molecule;
   (d) a ratio of guar gum material to carboxyvinyl polymer of from about 2.5:1 to about 1:2.5; and
   (e) water.

2. The liquid cleansing product of claim 1 wherein said monomeric monoolefinically-unsaturated carboxylic acid is a monomeric monoolefinic acrylic acid of the structure

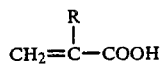

where R is a substituent selected from the class consisting of hydrogen and lower alkyl groups, and wherein said polyol is an oligosaccharide.

3. The liquid cleansing product of claim 1 wherein said monomeric monoolefinically-unsaturated carboxylic acid is acrylic acid, and wherein said polyol is sucrose.

4. The liquid cleansing product of claim 3 wherein said polyether of sucrose comprises from about 0.2% to about 2.5% by weight of the total monomers.

5. The liquid cleansing product of claim 3 wherein said polyether of sucrose comprises about 1% by weight of the total monomers and wherein said sucrose has at least about five allyl ether groups per sucrose molecule.

6. The liquid cleansing product of claim 5 wherein said carboxyvinyl polymer has molecular weight of at least about 1,250,000.

7. The liquid cleansing product of claim 1 wherein said guar gum material is hydroxypropyl guar gum having a degree of substitution of less than about 1.2.

8. The liquid cleansing product of claim 3 wherein said guar gum material is hydroxypropyl guar gum having a degree of substitution of less than about 1.2.

9. The liquid cleansing product of claim 4 wherein said guar gum material is hydroxypropyl guar gum having a degree of substitution of from about 0.3 to about 0.8.

10. The liquid cleansing product of claim 5 wherein said guar gum material is hydroxypropyl guar gum having a degree of substitution of from about 0.3 to about 0.8.

11. The liquid cleansing product of claim 1 wherein said guar gum material is hydroxypropyl guar gum having a degree of substitution of about 0.6.

12. The liquid cleansing product of claim 6 wherein said guar gum material is hydroxypropyl guar gum having a degree of substitution of about 0.6.

13. The liquid cleansing product of claim 1 wherein said surfactant is selected from the group consisting of anionic and nonionic detergents, and mixtures thereof.

14. The liquid cleansing product of claim 9 wherein said surfactant is selected from the group consisting of anionic and nonionic detergents, and mixtures thereof.

15. The liquid cleansing product of claim 1 wherein said surfactant is selected from the group consisting of alkali metal and ammonium alkyl sulfate, alkali metal and ammonium alkyl ethoxy sulfate, and the monoethanol and diethanol amides of fatty acids, and mixtures thereof.

16. The liquid cleansing product of claim 9 wherein said surfactant is selected from the group consisting of alkali metal and ammonium alkyl sulfate, alkali metal and ammonium alkyl ethoxy sulfate, and the monoethanol and diethanol amides of fatty acids, and mixtures thereof.

17. The liquid cleansing product of claim 10 wherein said surfactant is selected from the group consisting of sodium alkyl sulfate, sodium alkyl ethoxy(3) sulfate, and coconut monoethanol amide, and mixtures thereof.

18. The liquid cleansing product of claim 1 wherein said cleansing product comprises from about 10% to about 30% of said surfactant, from about 0.2% to about 0.5% of said guar gum material, and from about 0.2% to about 0.5% of said carboxyvinyl polymer.

19. The liquid cleansing product of claim 14 wherein said cleansing product comprises from about 10% to about 30% of said surfactant, from about 0.2% to about 0.5% of said guar gum material, and from about 0.2% to about 0.5% of said carboxyvinyl polymer.

20. The liquid cleansing product of claim 17 wherein said cleansing product comprises from about 10% to about 30% of said surfactant, from about 0.2% to about 0.5% of said guar gum material, and from about 0.2% to about 0.5% of said carboxyvinyl polymer.

21. The liquid cleansing product of claim 19 wherein said cleansing product comprises from about 15% to about 25% of said surfactant.

22. The liquid cleansing product of claim 11 wherein said carboxyvinyl polymer comprises polyacrylic acid cross-linked with about 1% of polyallyl sucrose having an average of about 5.8 allyl groups for each sucrose molecule, said carboxyvinyl polymer having a high molecular weight.

23. The liquid cleansing product of claim 22 wherein said surfactant is selected from the group consisting of alkali metal and ammonium alkyl sulfate, alkali metal and ammonium alkyl ethoxy sulfate, and the monoethanol and diethanol amides of fatty acids, and mixtures thereof.

24. The liquid cleansing product of claim 23 wherein said cleansing product comprises from about 10% to about 30% of said surfactant, from about 0.2% to about 0.5% of said guar gum material, and from about 0.2% to about 0.5% of said carboxyvinyl polymer.

25. The liquid cleansing product of claim 1 wherein said carboxyvinyl polymer comprises polyacrylic acid cross-linked with about 1% of polyallyl sucrose having an average of about 5.8 allyl groups for each sucrose molecule, said carboxyvinyl polymer having a high molecular weight.

* * * * *